United States Patent [19]

Baum et al.

[11] Patent Number: 5,783,716
[45] Date of Patent: Jul. 21, 1998

[54] PLATINUM SOURCE COMPOSITIONS FOR CHEMICAL VAPOR DEPOSITION OF PLATINUM

[75] Inventors: Thomas H. Baum, New Fairfield; Peter S. Kirlin; Sofia Pombrik, both of Bethel, all of Conn.

[73] Assignee: Advanced Technology Materials, Inc., Danbury, Conn.

[21] Appl. No.: 673,372

[22] Filed: Jun. 28, 1996

Related U.S. Application Data

[60] Provisional application No. 60/00,764 Jun. 30, 1995.

[51] Int. Cl.$^6$ .................................................. C07F 15/00
[52] U.S. Cl. .................................... 556/136; 427/587
[58] Field of Search ................................... 556/136

[56] References Cited

U.S. PATENT DOCUMENTS

| | | | |
|---|---|---|---|
| 5,104,684 | 4/1992 | Tao et al. | 427/38 |
| 5,130,172 | 7/1992 | Hicks et al. | 427/252 |
| 5,280,012 | 1/1994 | Kirlin et al. | 501/1 |
| 5,403,620 | 4/1995 | Kaesz et al. | 427/252 |

OTHER PUBLICATIONS

Koplitz, Lynn Vogel et al.; "Laser–Driven Chemical Vapor Deposition of Platinum at Atmospheric Pressure and Room Temperature from CpPt(CH$_3$)$_3$," Appl. Phys. Lett. 53(18),31 Oct. 1988, pp. 1705–1707.

Chen, Yea–jer et al.,"Low–Temperature Organometallic Chemical Vapor Deposition of Platinum."Appl. Phys. Lett. 53(17), 24 Oct. 1988, pp. 1591–1592/.

Xue, Ziling et al.,"Organometallic Chemical Vapor Deposition of Platinum. Reaction Kinetics and Vapor Pressures of Precursors." Chem. Mater. 1992,4, pp. 162–166.

Dryden, Neil H. et al.,"Chemical Vapor Deposition of Platinum: New Precursors and Their Properties."Chem. Mater. 1991,3, pp. 677–685.

Xue, Ziling et al.,"Characterization of(Methylcyclopentadienyl)trimethylplatinum and Low–Temperature Organometallic Chemical Vapor Depositon of Platinum Metal."J. Am. Chem. Soc., 1989, III,8779–8784.

Zin, Alfred A. et al.,"Chemical Vapor Deposition of Platinum, Palladium and Nickel," chapter 7 of *The Chemistry of Metal CVD*,T. Kodas et al., editors, VCH Publishers, New York, 1994, pp. 329–355.

Rand. M.J., Electronchem. Soc., 1973, 120, p. 686.
Kumar, R., et al., Polyhedron, 1989,8,p. 551.

*Primary Examiner*—Porfirio Nazario–Gonzalez
*Attorney, Agent, or Firm*—Oliver A. Zitzmann; Steven J. Hultquist

[57] ABSTRACT

A platinum source reagent liquid solution, comprising:
  (i) at least one platinum source compound selected from the group consisting of compounds of the formulae:
     (A) RCpPt(IV)R'$_3$ compounds, of the formula:

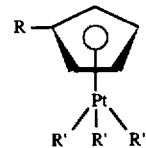

wherein:
  R is selected from the group consisting of hydrogen, methyl, ethyl, i-propyl, n-propyl, n-butyl, i-butyl, t-butyl, trimethylsilyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl; and (B) Pt(β-diketonates)$_2$ of the formula:

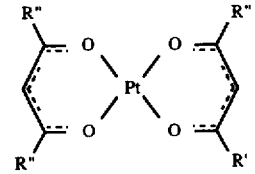

wherein:
  each R" is independently selected from the group consisting of methyl, ethyl, n-propyl, i-propyl, n-butyl, i-butyl, t-butyl, trifluoromethyl, perfluoroethyl, and perfluoro-n-propyl, and (ii) a solvent medium therefor.

The platinum source reagent liquid solutions of the invention are readily employed in a chemical vapor deposition process system including a liquid delivery apparatus for volatilizing the source reagent liquid solution and transporting the resulting vapor to the chemical vapor deposition reactor for deposition of platinum on a substrate mounted in the CVD reactor.

11 Claims, No Drawings

PLATINUM SOURCE COMPOSITIONS FOR CHEMICAL VAPOR DEPOSITION OF PLATINUM

CROSS-REFERENCE TO RELATED APPLICATION

This application claims priority under 35 U.S.C.§119 of U.S. Provisional Patent Application Ser. No. 60/000,764 filed Jun. 30, 1995 in the names of Thomas H. Baum, Peter S. Kirlin, and Sofia Pombrik for "Platinum Source Compositions for Chemical Vapor Deposition of Platinum."

BACKGROUND OF THE INVENTION

1. Field of the Invention

This invention relates to the formation by chemical vapor deposition of platinum and platinum-containing films, using source reagent solution compositions of platinum-containing source compounds and complexes.

2. Description of the Related Art

Ferroelectric thin films formed of oxide compositions such as strontium bismuth tantalate ($SrBi_2Ta_xO_y$) are potentially useful as capacitor materials for the fabrication of microelectronic devices such as dynamic random access memory (DRAM) devices.

Various means and methods for deposition formation of such ferroelectric films have come into use or otherwise been proposed in the art, including sol-gel, spray pyrolysis, aerosol and liquid delivery chemical vapor deposition (CVD) techniques. The CVD approach is particularly advantageous because it enables high aspect ratio features to be efficiently coated and conformal films to be deposited over non-planar surface topographies.

In the fabrication of DRAM (as well as FRAM) devices, platinum metal (Pt) often is utilized as an electrode for the device. It would be desirable to form the platinum films by CVD as well, to integrate the manufacturing steps efficiently.

The chemical vapor deposition of Pt films over small-scale, localized areas has been carried out successfully using various solid precursors, including for example tetrakis (trifluorophosphine) platinum, bis(β-diketonate) platinum, (cyclopentadienyl) platinum trimethyl, and (alkylcyclopentadienyl) platinum trimethyl, and inducing deposition of the platinum over the localized area by focused ion beam, electron beam, or laser decomposition of the platinum precursor. This technique may be used for, e.g., formation of platinum interconnects, microsurgery to correct subsurface chip defects, or repair of x-ray masks, as described in Tao and Melngailis, U.S. Pat. No. 5,104,684, "Ion Beam Induced Deposition of Metals." In general, such precursor compounds have superior volatility characteristics, being readily volatilized by sublimation from the solid phase in conventional bubbler-based transport systems for subsequent chemical vapor deposition in the deposition reactor. In consequence, the use of such conventional bubbler-based transport systems for forming the vapor of these solid precursors for platinum has proven sufficiently advantageous in terms of the rate of transport of the platinum source vapor to the downstream CVD reactor, so that alternative delivery techniques have not been actively sought.

However, when it is desired to form larger area platinum films with continuous coverage of surfaces of various geometries, there are suggestions that mass transport of these platinum reagents to the deposition reactor may be inadequate. For example, as reported in "Chemical Vapor Deposition of Platinum, Palladium and Nickel," Alfred A. Zinn, et al., in The Chemistry of Metal CVD, edited by Toivo T. Kodas and Mark J. Hampden-Smith, VCH Verlagsgesellschaft mbH, Weinheim, Germany and VCH Publishers Inc., New York, p. 337, low growth rates of platinum were reported and attributed to "an inadequate supply of the precursor to the reactor."

Examples of prior art CVD-based platinum deposition process technology include the compositions and coating formation technology disclosed in U.S. Pat. No. 5,130,172 issued Jul. 14, 1992 to Robert F. Hicks, et al. and U.S. Pat. No. 5,403,620 issued Apr. 4, 1995 to Herbert D. Kraesz, et al., which teach to form a platinum coating on a substrate from organometallic compounds such as (trimethyl) (cyclopentadienyl)platinum in the presence of a reducing fluid such as hydrogen gas.

In general, the transport rate of source reagent vapor to the CVD reactor in CVD process systems has a substantial impact on the ease and economics of operating such systems, and a means and method which markedly increases such transport rate of the reagent source material to the CVD reactor represents a significant advance in the art of chemical vapor deposition.

It therefore is an object of the present invention to provide an improved composition, means, and method for delivery of platinum source material to the reactor of a chemical vapor deposition process system.

It is another object of the invention to provide an improved Pt CVD process, which provides faster film growth rates via liquid delivery and eliminates the deleterious effects of having hydrogen in contact with capacitor "oxides" at elevated temperatures (i.e., ≧500° C.), when Pt electrodes or other Pt thin film structures are formed on oxide substrates, as hereinafter more fully disclosed.

Other objects, features and advantages of the present invention will be more fully apparent from the ensuing disclosure and appended claims.

SUMMARY OF THE INVENTION

The present invention broadly relates in a compositional aspect to a platinum source reagent liquid solution, comprising:

(i) at least one platinum source compound selected from the group consisting of compounds of the formulae:
(A) RCpPt(IV)R'$_3$ compounds, of the formula:

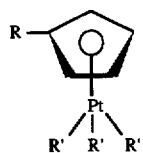

wherein:

R is selected from the group consisting of hydrogen, methyl, ethyl, i-propyl, n-propyl, n-butyl, i-butyl, t-butyl, trimethylsilyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl; and (B) Pt(β-diketonates)$_2$ of the formula:

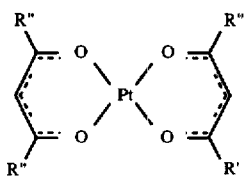

wherein:
   each R" is independently selected from the group consisting of methyl, ethyl, n-propyl, i-propyl, n-butyl, i-butyl, t-butyl, trifluoromethyl, perfluoroethyl, and perfluoro-n-propyl, and
   (ii) a solvent medium therefor.

The solvent medium in such solution may for example comprise one or more solvent species selected from the group consisting of hydrocarbons, ethers, alcohols and esters.

In a method aspect, the present invention relates to a process for forming a platinum coating on a substrate in a chemical vapor deposition reactor, comprising the steps of:
   (a) providing a platinum source reagent liquid solution, comprising:
      (i) at least one platinum source compound selected from the group consisting of compounds of the formulae:
         (A) RCpPt(IV)R'$_3$ compounds, of the formula:

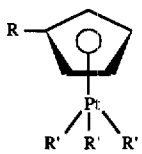

wherein:
         R is selected from the group consisting of hydrogen, methyl, ethyl, i-propyl, n-propyl, n-butyl, i-butyl, t-butyl, trimethylsilyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl; and
         (B) Pt(β-diketonates)$_2$ of the formula:

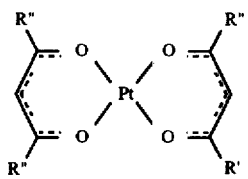

wherein:
         each R" is independently selected from the group consisting of methyl, ethyl, n-propyl, i-propyl, n-butyl, i-butyl, t-butyl, trifluoromethyl, perfluoroethyl, and perfluoro-n-propyl, and
         (ii) a solvent medium therefor;
   (b) volatilizing the platinum source reagent liquid solution to form a platinum source reagent vapor therefrom;
   (c) transporting the platinum source reagent vapor to a chemical vapor deposition reactor; and
   (d) depositing platinum from the platinum source reagent vapor on the substrate in the chemical vapor deposition reactor, under chemical vapor deposition conditions effective therefor.

Such chemical vapor deposition conditions may advantageously comprise the presence of an oxidizing gas, e.g., oxygen (O$_2$), ozone (O$_3$), nitrous oxide (N$_2$O) or mixtures thereof, particularly when the substrate comprises a perovskite oxide. Alternatively, the chemical vapor deposition conditions may advantageously comprise the presence of a reducing gas, e.g., H$_2$ or NH$_3$, when such reducing gas is beneficial to the Pt deposition process, or otherwise does not preclude the efficacy of the process or the deposited Pt film for their intended purpose.

In a preferred aspect, the volatilization and transport of the platinum source reagent may be effected by a liquid delivery system of the type as variously disclosed in U.S. Pat. No. 5,204,314 and pending U.S. Pat. application Ser. No. 08/280,143 filed Jul. 25, 1994 and issued Jul. 16, 1996 as U.S. Pat. No. 5,536,323, and pending U.S. patent application Ser. No. 08/484,025 filed Jun. 7, 1995 in the names of Peter S. Kirlin, Robin L. Binder, Robin A. Gardiner, Peter Van Buskirk, Jiming Zhang, and Gregory Stauf, for "Source Reagent Liquid Delivery Apparatus, and Chemical Vapor Deposition System Comprising Same," the disclosures of which hereby are incorporated herein by reference in their entirety.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention is based on the surprising and unexpected discovery that a liquid delivery approach to the transport of a platinum source reagent to a CVD reactor, using a source reagent liquid solution which is volatilized to provide a vapor phase platinum source material for subsequent deposition from the vapor in the CVD reactor of platinum, can provide a high level of improvement, e.g., of 10–100 times relative to the use of conventional bubbler-based reagent delivery to the CVD reactor, in faster film growth rates and higher manufacturing process throughput of deposition substrates and output of CVD product articles.

In one preferred aspect, the liquid delivery method of the present invention is carried out in a manner at odds with the prevailing approach in the art for effecting CVD of platinum. As discussed earlier in the "Background of the Invention" section hereof, Hicks et al. U.S. Pat. No. 5,130,172 and Kraesz, et al. U.S. Pat. No. 5,403,620 teach to form a platinum coating on a substrate from organometallic compounds such as (trimethyl)(cyclopentadienyl)platinum in the presence of a reducing fluid such as hydrogen gas.

The Hicks et al. '172 and Kraesz, et al. '620 patents, together with the published literature in the field of platinum film formation technology, provide a "conventional wisdom" consensus that reducing gases, such as hydrogen (H$_2$) and forming gases (H$_2$ in inert gases such as helium, nitrogen and argon) are necessary for high-purity Pt film growth. In fact, the applicants have determined that the presence and reactivity of hydrogen with complex perovskite oxides, e.g., in the CVD formation of conducting platinum electrodes on perovskite "oxide" capacitors, in accordance with the teachings of the Hicks et al. '172 and Kraesz, et al. '620 patents, can actually be detrimental to the deposited capacitor or ferroelectric thin-film.

The present invention thus contemplates an improved Pt CVD process, which provides faster film growth rates via liquid delivery and eliminates the deleterious effects of having hydrogen in contact with capacitor "oxides" at elevated temperatures (i.e., ≥500° C.), in relation to the prior art Pt film formation processes. In instances where the substrate and overall process are benefitted or at least not unduly adversely affected by the presence of a reducing gas in the chemical vapor deposition chamber, a reducing gas may be employed. Thus, the invention comtemplates that the vapor phase composition in the chemical vapor deposition step may potentially comprise other vapor or gas phase constituents, including reducing and oxidizing gas/vapor species, and/or any other species which are advantageously present in the CVD step or at least do not preclude the efficacy of such step in deposition of Pt-containing film material.

It is a preferred aspect of the present invention, however, to utilize an oxidizing gas in the CVD step when depositing Pt on substrates containing perovskite oxide components, or other substrate materials which are deleteriously affected by the presence of a reducing gas in the CVD reactor.

In such aspect, the present invention improves on the current Pt CVD processes of the Hicks et al. and Kraesz et al. patents, and such conventional wisdom prior art approach, by applicants' use of oxidizer gas(es) such as oxygen ($O_2$), ozone ($O_3$), nitrous oxide ($N_2O$), and mixtures thereof, in the Pt CVD process. The use of oxidizer gases during Pt CVD and electrode thin-film formation has several advantages including, but not limited to:

1. oxidation of carbon-containing ligands and decomposition by-products of the precursor and the solvent, providing high-purity, near-bulk resistivities.
2. oxidation of the Pt-perovskite interfacial region during nucleation and steady state film growth. This ensures that the surface of the complex oxide capacitor film is not deteriorated in an adverse manner in respect of film stoichiometry, capacitance, dielectric constant, capacitance per area, and device performance.
3. Pt thin films readily allow oxygen diffusion throughout the metal layer at elevated temperatures and thereby ensure carbon removal in the film, at the interface, thereby obviating the concerns stated in the preceding paragraph.
4. The use of oxygen/nitrous oxide provides a useful manufacturing scheme for thin film growth of Pt electrodes via a liquid delivery methodology to perovskite based thin-film capacitors. Such process is highly suitable for DRAM device production.

The platinum source reagent compounds which have been found to be well suited to liquid delivery CVD of platinum in the broad practice of the invention include a wide variety of organoplatinum compounds and complexes, with platinum (II) bis(β-diketonates) and platinum (IV) (cyclopentadienyl) trialkyls being particularly preferred. In accordance with the invention, these platinum source compounds are dissolved at appropriate concentration in a suitable solvent medium, to form source reagent compound solutions. Illustrative Pt source compounds of the invention include:

(i) Pt (II) bis(1,1,1,5,5,5-hexafluoro-2,4-pentanedionato);
(ii) Pt (II) bis(2,2,6,6,-tetramethyl-3,5-heptanedionato);
(iii) Pt (IV) (methylcyclopentadienyl) trimethyl;
(iv) Pt(CO)$_2$Cl$_2$;
(v) Pt(acac)$_2$;
(vi) Pt(PF$_3$)$_4$;
(vii) Pt(CH$_3$)$_2$[(CH$_3$)NC];
(viii) (COD)Pt(CH$_3$)$_2$;
(ix) (COD)Pt(CH$_3$)($\eta^1$—C$_5$H$_5$);
(x) (COD)Pt(CH$_3$)Cl;
(xi) (C$_5$H$_5$)Pt(CH$_3$)(CO);
(xii) (C$_5$H$_5$)Pt(allyl)
(xiii) (acac)Pt(CH$_3$)$_3$;
(xiv) (C$_5$H$_5$)Pt(CH$_3$)$_3$;
(xv) (CH$_3$C$_5$H$_4$)Pt(CH$_3$)$_3$.

wherein: acac=acetylacetonate; C$_5$H$_5$=$\eta^5$-cyclopentadienyl; CH$_3$C$_5$H$_4$=$\eta^5$-methylcyclopentadienyl; COD=1,5-cyclooctadiene; and $\eta^1$-C$_5$H$_5$=$\eta^1$-cyclopentadienyl.

Illustrative Pt compounds which are potentially usefully employed in the broad practice of the invention include those described in Rand, M. J., J Electrochem. Soc. 1973, 120, 686; Kumar, R., et al., Polyhedron 1989, 8, 551; Dryden, N. H., et al., Chem. Mater. 1991, 3, 677; Xue, Z., et al., Chem. Mater., 1992, 4, 162; Chen, Y. J., et al., Appl. Phys. Lett. 1988, 53, 1591; and Xue, Z., et al., J Am. Chem. Soc., 1989, 111, 8779.

The above-identified platinum source reagent compounds are exceedingly soluble in hydrocarbons, ethers, alcohols and ester solvents, and can be utilized in high concentrations in the solutions of the invention. Illustrative solvent species which may potentially be usefully employed singly or in mixtures in the practice of the invention include n-butyl acetate, tetraglyme, isopropanol, tetrahydrofuran, hexane, heptane, octane, etc. Some illustrative specific solvent composition species include:

(i) a mixture of n-butyl acetate and tetraglyme, (ii) a mixture of tetrahydrofuran and tetraglyme;

(iii) a mixture of n-butyl acetate and isopropanol;

(iv) a mixture of tetrahydrofuran, isopropanol, and tetraglyme; and (v) n-octane.

The platinum source reagent compound solutions of the invention have demonstrated utility for the deposition of high-purity platinum films and conductive layers. The physical and chemical properties of the source reagent compositions and resulting films achieved in the broad practice of the invention can be dramatically altered by small changes in the molecular structure of the source reagent compounds.

For example, the melting point of (MeCp) Pt Me$_3$ is 29°–30° C. while the non-methylated analog (Cp) Pt Me$_3$ melts at 108° C. As a further example, substitution of the Me groups in (MeCp) Pt Me$_3$ with ethyl (Et) groups yields corresponding liquid complexes. Similarly, fluoro substitution of platinum (II) bis(β-diketonates) leads to lower melting complexes with greatly enhanced volatilities. The solubility of the these derivatives is higher than the analogous non-fluorinated platinum source reagent materials. It will therefore be apparent that the compositions of the invention can be readily tailored to achieve high growth rates of platinum films by increased volatility and solubility of the platinum precursors in organic media.

The platinum source reagent compounds usefully employed in liquid source reagent solutions according to the invention include source compounds of the formulae set out below:

(A) RCpPt(IV)R'$_3$ compounds, of the formula:

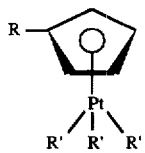

wherein:

R is selected from the group consisting of hydrogen, methyl, ethyl, i-propyl, n-propyl, n-butyl, i-butyl, t-butyl, trimethylsilyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl; and (B) Pt(β-diketonates)$_2$ of the formula:

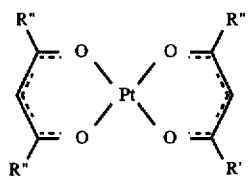

wherein:

each R" is independently selected from the group consisting of methyl, ethyl, n-propyl, i-propyl, n-butyl, i-butyl, t-butyl, trifluoromethyl, perfluoroethyl, and perfluoro-n-propyl.

The above-described liquid solution compositions of the invention may be advantageously employed for forming a platinum coating on a substrate in a chemical vapor deposition reactor, by volatilizing the platinum source reagent liquid solution to form a platinum source reagent vapor therefrom, and transporting the resulting platinum source reagent vapor to a chemical vapor deposition reactor. In the CVD reactor, the platinum is deposited from the platinum source reagent vapor on the substrate, under suitable chemical vapor deposition conditions, such as may readily be determined without undue experimentation by those of ordinary skill in the art. Such chemical vapor deposition conditions may for example comprise the presence of an oxidizing gas, and (contrary to the teachings of the Hicks et al. +172 and Kraesz, et al. +620 patents) the absence of hydrogen or other reducing gases. Alternatively, as discussed hereinabove, the chemical vapor deposition conditions may include the presence of a reducing gas species, e.g., hydrogen, ammonia, etc.

The substrate may be of any suitable type and composition, and may for example comprise insulating, dielectric, conducting, semiconducting, etc., materials, or combinations thereof. The substrate may for example comprise a semiconductor substrate with a device or other architecture or structure thereon, with respect to which the Pt material formed by the method of the invention forms a component or operative part. The substrate may for example comprise a perovskite oxide or other composition, and may comprise a diffusion barrier, wherein the diffusion barrier includes a material selected from the group consisting of titanium nitride, tantalum nitride, and titanium aluminum nitride.

The volatilization and transport of the platinum source reagent ma y be effected by a liquid deliver y system of any suitable type, as f or example a liquid delivery system and corresponding liquid delivery system operation as more fully disclosed in the aforementioned U.S. Pat. No. 5,204,314, U.S. Pat. No. 5,536,323 issued Jul. 16, 1996, and pending U.S. patent application Ser. No. 08/484,025 filed Jun. 7, 1995 in the names of Peter S. Kirlin, Robin L. Binder, Robin A. Gardiner, Peter Van Buskirk, Jiming Zhang, and Gregory Stauf, for "Source Reagent Liquid Delivery Apparatus, and Chemical Vapor Deposition System Comprising Same," the disclosures of all of which are incorporated herein by reference in their entirety.

The features and advantages of the invention are more fully illustrated by the following non-limiting examples, where in all parts and percentages are by weight, unless otherwise expressly stated.

EXAMPLE 1

A solution consisting of platinum (II) bis(1,1,1,5,5,5-hexafluoro-2,4-pentanedionato) was dissolved in an organic solvent (hydrocarbon, alcohol, ether, ester). The solution was delivered to a warm-walled reactor using a liquid delivery system and thermally decomposed in an $O_2/N_2O$ mixture to deposit a Pt film. This film can be used as an electrode for DRAM applications or as a catalytic surface for subsequent reaction.

EXAMPLE 2

A solution consisting of platinum (II) bis(2,2,6,6,-tetramethyl-3,5-heptanedionato) was dissolved in a solution of n-butyl acetate and tetraglyme (25:1). This solution was delivered, using a commercial liquid delivery system, to a warm walled CVD reactor in an $O_2/N_2O$ mixture to deposit thin, electrically conductive Pt films. These films can be used as circuits or electrodes for a variety of microelectronic applications.

EXAMPLE 3

In a modification to Example 1 and 2, a solution consisting of platinum (II) bis (2,2,6,6,-tetramethyl-3,5-heptanedionato) was dissolved in a solution of tetrahydrofuran and tetraglyme (25:1). This solution was delivered (using a commercial liquid delivery system) to a CVD reactor to produce high quality Pt films. The decomposition was performed in the presence of $O_3$ or $O_2/N_2O$ mixture to facilitate clean decomposition of the Pt source.

EXAMPLE 4

In a modification to Examples 3, platinum (II) bis(2,2,6,6,-tetramethyl-3,5-heptanedionato) was dissolved in a solution of n-butyl acetate and isopropanol. The presence of the alcohol co-reactant facilitates the decomposition and liberation of protonated 2,2,6,6,-tetramethyl-3,5-heptanedione. The need for $O_3$ or $O_2/N_2O$ mixture provide carbon-free films and ensures the capacitor thin-film properties for manufacturing.

EXAMPLE 5

A solution consisting of platinum (IV) (methylcyclopentadienyl) trimethyl was dissolved in an organic solvent (hydrocarbon, ether, ester). The solution was delivered to a warm-walled reactor using a commercial liquid delivery system and thermally decomposed to deposit a Pt film. This approach enables faster film growth rates to be realized by increasing the mass-transport of reactant to the heated substrate surface and therefore, is of greater utility than using conventional bubbler systems. The deposited Pt film can be used as an electrode for DRAM applications, as an electrical conductor or as a catalytic surface for subsequent reaction (i.e. hydrosilylation, polymerization or hydrogenation).

EXAMPLE 6

In a modification of example 5, a solution of platinum (IV) (methylcyclopentadienyl) trimethyl was dissolved in a hydrocarbon solvent, such as n-octane (0.25M) and delivered to a warm-walled reactor using a commercial liquid delivery system. Thermal decomposition to deposit a Pt film was realized using substrate temperature between 200° and 300° C. in the presence of an $O_2/N_2O$ mixture. This approach enables fast film growth rates to be realized via increased mass-transport of reactant to the heated substrate surface and the deposited Pt film can be used as an electrode for DRAM applications or as a catalytic surface for subsequent reaction (i.e. hydrosilylation, polymerization or hydrogenation, etc.).

EXAMPLE 7

In a modification of examples 4 and 5, a solution of platinum (IV) (cyclopentadienyl) trimethyl was dissolved in a hydrocarbon solvent (0.25M) and delivered to a warm-walled reactor using a commercial liquid delivery system. Thermal decomposition to deposit a Pt film electrode was realized using substrate temperature between 500° and 700° C. in the presence of an $O_2/N_2O$ mixture. This approach enables faster film growth rates to be realized via increased mass-transport of reactant to the heated substrate surface and the deposited Pt film provides superior performance as an electrode for DRAM applications. The integrity of the DRAM perovskite capacitor film is preserved in the presence of the oxidizing co-reactants ($O_2/N_2O$ mixture) during Pt CVD.

EXAMPLE 8

A solution consisting of platinum (II) bis(1,1,1,5,5,5-hexafluoro-2,4-pentanedionato) was dissolved in an organic solvent containing tetrahydrofuran, i-propanol and tetraglyme (8:2:1). The solution was delivered to a warm-walled reactor using a liquid delivery system and reacted with $O_2/N_2O$ mixture to produce a conductive Pt film. In a modification of this method, a co-reactant (i.e., $O_3$) were used to facilitate the decomposition reaction and formation of pure Pt films. This approach can be used to produce conducting circuits and electrodes for microelectronic applications (i.e., DRAMs).

EXAMPLE 9

A solution consisting of platinum (II) bis(1,1,1,5,5,5-hexafluoro-2-,4-pentanedionato) was dissolved in an organic solvent containing tetrahydrofuran and tetraglyme (10:1). The solution was delivered to a warm-walled reactor using a commercial liquid delivery system and reacted with $H_2$ produce a pure platinum film. The selective deposition of Pt onto metallic surfaces can be realized after using a chemical pre-treatment or plasma treatment to modify the surface properties of the substrate. The observed selectivity is enhanced after pre-treatment of the substrate. In this manner the selective formation of conductive circuits or electrodes may be realized for DRAM or FRAM applications.

EXAMPLE 10

In a modification of examples 4, 5 and 6, a solution of platinum (IV) (cyclopentadienyl) trimethyl was dissolved at lower concentrations (0.05–0.15M) hydrocarbon solvent (n-octane) and delivered to a warm-walled reactor using a commercial liquid delivery system. Thermal decomposition to deposit a Pt film electrode was realized using substrate temperature between 500° and 700° C. in the presence of an $O_2/N_2O$ mixture. This approach enables slower film growth rates to be realized and provides controlled film orientation in thin ($\leq$200 nm) films. The deposited Pt film provides superior performance as an electrode for DRAM applications. The integrity of the DRAM perovskite capacitor film is preserved in the presence of the oxidizing co-reactants ($O_2/N_2O$ mixture) during Pt CVD.

While the present invention has been illustratively described herein with reference to specific aspects, features and embodiments, it will be recognized that the invention is not thus limited, but rather encompasses within its scope, alternative variations, modifications, and other embodiments, and the invention therefore is intended to be broadly construed to include within its spirit and scope of all such variations, modifications and embodiments.

What is claimed is:

1. A platinum source reagent liquid solution, comprising:
   (i) at least one platinum source compound selected from the group consisting of compounds of the formulae:
   (A) $RCpPt(IV)R'_3$ compounds of the formula:

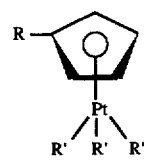

wherein:
   R is selected from the group consisting of hydrogen, methyl, ethyl, i-propyl, n-propyl, n-butyl, i-butyl, t-butyl, trimethylsilyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl; and
   (B) $Pt(\beta\text{-diketonates})_2$ of the formula:

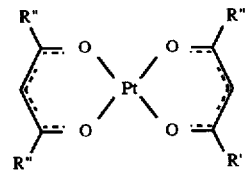

wherein:
   each R" is independently selected from the group consisting of methyl, ethyl, n-propyl, i-propyl, n-butyl, i-butyl, t-butyl, trifuromethyl, perfluoroethyl, and perfluoro-n-propyl, and
   (ii) a solvent medium therefor, subject to the proviso that when R and all R' are methyl, the solvent is not $CDCl_3$.

2. A platinum source reagent liquid solution according to claim 1, wherein the solvent medium comprises one or more solvent species selected from the group consisting of hydrocarbons, ethers, alcohols and esters.

3. A platinum source reagent liquid solution according to claim 1, wherein the platinum source compound is selected from the group consisting of platinum (II) bis($\beta$-diketonates) and platinum (IV) (cyclopentadienyl) trialkyls.

4. A platinum source reagent liquid solution according to claim 1, wherein the solvent is selected from the group consisting of n-butyl acetate, tetraglyme, isopropanol, tetrahydrofuran, hexane, heptane, and octane.

5. A platinum source reagent liquid solution according to claim 1, wherein the solvent is selected from the group consisting of:

(i) a mixture of n-butyl acetate and tetraglyme;

(ii) a mixture of tetrahydrofuran and tetraglyme;

(iii) a mixture of n-butyl acetate and isopropanol;

(iv) a mixture of tetrahydrofuran, isopropanol, and tetraglyme; and (v) n-octane.

6. A platinum source reagent liquid solution, wherein the platinum source compound is selected from $RCpPt(IV)R'_3$ compound of the formula:

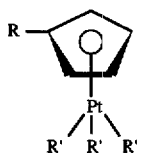

wherein:

R is selected from the group consisting of hydrogen, methyl, ethyl, i-propyl, n-propyl, n-butyl, i-butyl, t-butyl, trimethyl silyl and trimethylsilyl methyl; and each R' is independently selected from the group consisting of methyl, ethyl, i-propyl, n-propyl, n-butyl, i-butyl, t-butyl, trimethylsilyl and trimethylsilyl methyl;

subject to the proviso that when R and all R' are methyl, the solvent is not $CDCl_3$.

7. A platinum source reagent liquid solution according to claim 1, wherein the platinum source compound is selected from $Pt(\beta\text{-diketonates})_2$ of the formula:

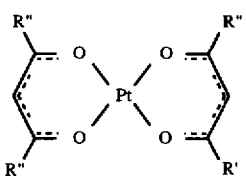

wherein:

each R" is independently selected from the group consisting of methyl, ethyl, n-propyl, i-propyl, n-butyl, i-butyl, t-butyl, trifluoromethyl, perfluoroethyl, and perfluoro-n-propyl.

8. A platinum source reagent liquid solution according to claim 1, wherein the platinum source compound is selected from the group consisting of:

(i) platinum (II) bis(1,1,1,5,5,5-hexafluoro-2,4-pentanedionato);

(ii) platinum (II) bis(2,2,6,6,-tetramethyl-3,5-heptane-dionato); and (iii) platinum (IV) (methylcyclopentadienyl)trimethyl.

9. A platinum source reagent liquid solution according to claim 1, wherein the platinum source compound is platinum (II) bis(1,1,1,5,5,5-hexafluoro-2,4-pentanedionato) and the solvent comprises at least one solvent species selected from the group consisting of tetraglyme, tetrahydrofuran, and isopropanol.

10. A platinum source reagent liquid solution according to claim 1, wherein the platinum source compound is platinum (II) bis(2,2,6,6,-tetramethyl-3,5-heptane-dionato) and the solvent comprises at least one solvent species selected from the group consisting of n-butyl acetate, tetraglyme, tetrahydrofuran, and isopropanol.

11. A platinum source reagent liquid solution according to claim 1, wherein the platinum source compound is platinum (IV) (methylcyclopentadienyl)trimethyl) and the solvent comprises n-octane.

* * * * *